United States Patent [19]

Shibayama et al.

[11] Patent Number: 4,613,573
[45] Date of Patent: Sep. 23, 1986

[54] AUTOMATIC BACTERIAL COLONY TRANSFER APPARATUS

[75] Inventors: Katsujiro Shibayama; Fukuo Iwaya, both of Tokyo; Kensaku Takahashi, Hiratsuka; Masumi Nukumi, Ome; Tatuhito Tuji, Uji; Michio Okuma, Tokyo; Yoji Odawara, Hitachi, all of Japan

[73] Assignees: Hitachi, Ltd., Tokyo; Hitachi Electronics Engineering Co., Ltd., Kanagawa, both of Japan

[21] Appl. No.: 495,489

[22] Filed: May 17, 1983

[30] Foreign Application Priority Data

May 20, 1982 [JP] Japan .................................. 57-84011
Jul. 12, 1982 [JP] Japan .................................. 57-119739

[51] Int. Cl.⁴ ........................ C12M 1/36; C12M 1/00; C12M 1/12; C12M 1/26
[52] U.S. Cl. .................................... 435/289; 435/287; 435/311; 435/808; 435/30; 435/292; 356/244
[58] Field of Search ............... 435/292, 293, 289, 291, 435/311, 808, 30, 3, 287; 422/67, 100; 356/244; 358/101; 364/188, 189, 146; 414/744 R

[56] References Cited

U.S. PATENT DOCUMENTS

| | | | |
|---|---|---|---|
| 3,666,629 | 5/1972 | Moore | 435/292 X |
| 3,935,075 | 1/1976 | Perry et al. | 435/293 |
| 4,115,200 | 9/1978 | Anderson | 435/293 |
| 4,213,825 | 7/1980 | Saxholm | 435/291 |
| 4,235,971 | 11/1980 | Howard et al. | 435/311 X |
| 4,242,462 | 12/1980 | Thomas | 435/292 |
| 4,252,897 | 2/1981 | Axford et al. | 435/34 |
| 4,273,877 | 6/1981 | Anagnostopoulos | 435/292 X |
| 4,287,301 | 9/1981 | Astle | 435/292 X |
| 4,295,198 | 10/1981 | Copeland et al. | 364/189 X |
| 4,383,041 | 5/1983 | Kutsusawa et al. | 435/291 |
| 4,397,955 | 8/1983 | Entis et al. | 435/292 |
| 4,480,031 | 10/1984 | Shaw | 435/292 X |

FOREIGN PATENT DOCUMENTS 0008792  3/1978  Japan .................................. 435/293

Primary Examiner—Robert J. Warden
Assistant Examiner—Randall E. Deck
Attorney, Agent, or Firm—Antonelli, Terry & Wands

[57] ABSTRACT

An apparatus for automatically transferring a desired one of bacterial colonies grown in a medium in a culture Petri dish onto a medium in a test Petri dish or a test tube by using a bacterial colony pick-up/transfer element of the disposable type or a bacterial colony pick-up/transfer element of the reuse type and by using various mechanisms controlled by a computer.

11 Claims, 23 Drawing Figures

AUTOMATIC BACTERIAL COLONY TRANSFER APPARATUS

The present invention relates to a bacterial colony transfer apparatus in which a colony of bacteria can be transferred from a culture Petri dish into a test Petri dish or into a test tube without any difficulties, and with only a visual inspecting operation being necessary for selecting a specific colony to be transferred.

A method of discovering effective bacteria in soil or the like has been used in order to develop new kinds of living things such as antibiotics. To this end, bacterial colonies are gathered or picked up from heterogeneous soil in wide areas and cultivated, through bacterial colony transferring operations between Petri dishes or between a Petri dish and a test tube. Further, in the field of genetic engineering in which various researches have been recently swiftly developed, a specific species of bacterium is selected and cultivated in expectation of creation of new living things by the gene recombination with the cultivated bacterium. Also in these processes, the bacterial colony transferring operations are frequently performed.

Conventionally, the bacterial colony transferring operation has been manually performed by using a platinum loop having a specially-shaped end such as an earpick-like tip, while visually inspecting the bacterial colony.

An example of the bacterial colony transferring operation, among many operation modes, is such that a bacterial colony which has grown to a certain extent, for example 1-2 mm or more in diameter, is selected among bacterial colonies growing gregariously in a medium of agar in a culture Petri dish and transferred to another Petri dish for test. This operation not only demands skill and is troublesome, considerably, but is complicated in recording and controlling various data as to the positions, kinds, or the like of the bacterial colony transferred.

As to the transferring operation modes in view of the kind of container into which a colony is transferred, it is the circumstance at present that a test Petri dish is suitable for the transfer of a bacterial colony including numbers of kinds of bacteria since its wide area is utilized, while a test tube is employed for cultivating a large number of bacteria of a single kind or one species.

Since it is important to prevent pollution by other various germs in the bacterial colony transferring operation, the operation is performed within a safety cabinet and all the instruments to be used are timely subjected to disinfection and sterilization (hereinafter represented merely by the term "sterilization"). If the bacterial colony transferring operation is viewed in a stage where study and development are performed, a process of picking out a new bacterial species which seems hopeful and useful while restricting to be a single species as pure as possible from a bacterial colony in which various species of bacteria are mixedly cultivated, and a process of performing pure culture of the picked out bacterial species are repeated. Where the new bacterial species is industrially mass produced or subject to registration and/or storage, a process of eliminating bacterial species which seem hardly useful and contaminated by various germs which should not exist thereat is performed. In actual cases it is necessary to handle several thousands or more test bodies every day. Accordingly, while the bacterial colony transferring operations seem simple at a glance, the operations in which the visual inspection for a long time for specifying a desired bacterial colony and the works for accurately picking up and transferring the specified bacterial colony are repeatedly performed thereby causing problems in that not only a person skilled at a certain extent is required but even such a skilled person becomes very tired. Further, there has been a problem that, as described above, the recording and storing the information with respect to the bacterial colony transfer is troublesome and inefficient.

An object of the present invention is to provide a bacterial colony transfer apparatus in which bacterial colony transferring operations can be automatically mechanically performed with the exception of the specific bacterial colony selecting operation which is manually performed under the present circumstances.

Recently, an apparatus for performing positioning with high accuracy becomes relatively easily available due to the remarkable development of so-called mechatronics, so that it has been made possible to reproduce an enlarged picture image of an objective bacterial colony on a display such as a cathode ray tube (CRT) by using a television camera instead of direct visual inspection of the objective bacterial colony so as to store in a storage device the coordinates of the position designated by, for example, a cursor on the display. Further, it is well known that not only lengthy, complicated sequential mechanism-control which could not be performed by mechanical means has been made possible to be very easily and very exactly performed today by using a computer, but also even the control processes can be easily changed and various kinds of computerized control apparatus becomes relatively inexpensive.

Another object of the present invention is to provide an automatic bacterial colony transfer apparatus in which a high accurate mechatronic technique and a computerized control technique as mentioned above are properly combined so that only the operation for selecting a desired bacterial colony is performed by visual inspection and the operations other than the colony selecting operation are automatically performed thereby making it possible to efficiently perform the whole bacterial colony transferring operations.

The foregoing and other objects and features of the present invention will become apparent from the following detailed description of preferred embodiments of the present invention when considered in conjunction with the accompanying drawings, in which.

Preferred embodiments of the present invention will be described hereunder. For convenience' sake, a Petri dish in which a gathered bacterial colony is cultivated is referred to as a culture Petri dish and a Petri dish into which a bacterial colony in the culture Petri dish is transferred is referred to as a test Petri dish, to thereby distinguish the respective Petri dishes from each other.

Conventionally, as described above, in the manual bacterial pick-up/transfer operations, the tip of the above-mentioned pre-washed and pre-sterilized platinum loop contacts a bacterial colony in a medium of a culture Petri dish so as to cause the colony to attach thereto, and thereafter the tip of the platinum loop contacts a medium in a test Petri dish or a test tube to thereby transfer the colony thereto.

The washing and sterilization of the platinum loop may be omitted during the continuous operations of transferring bacterial colonies of one and the same type or species. On the other hand, when the operation is restarted after interruption or where a bacterial colony of a different type or species from the type of species transferred immediately before is carried out, washing and sterilization are necessary. This should be applied to the case where automatization is effected in the same manner as mentioned above.

To this end, there are a first mode or reusing mode in which a platinum loop or the like to be used is subject to washing and sterilization and a second mode or disposable mode in which the washing and sterilization are omitted.

The platinum loop which is used in the first or reusing mode according to the present invention is well known and the description thereof is omitted and a pick-up of the self heating type according to the present invention will be described hereunder.

Figure 1A:
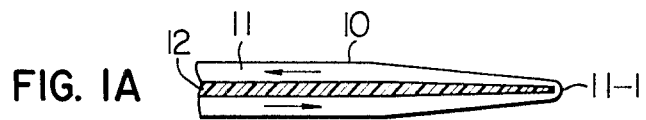
FIG. 1A is a cross-sectional view of an embodiment of a self heating type and portion of a pick-up section suitable for use in the apparatus according to the present invention.
Figure 1B:
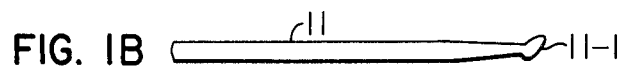
FIG. 1B is a side view of the embodiment of FIG. 1A.
Figure 1C:
FIG. 1C illustrates the energizing current of the end element of FIGS. 1A and 1B.
Figure 1D:
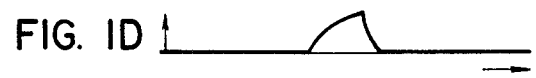
FIG. 1D illustrates the temperature of the end element of FIGS. 1A and 1B.

Referring now to the drawings wherein like reference numerals are used throughout the various views to designate like parts and, more particularly, to FIG. 1A, according to this figure a self heating type pick-up 10 is sterilized by self heating by a current conduction through the pick-up per se, with the pick-up 10 being fashioned of a heat-resisting wire such as, for example, a nichrome wire 11 folded in two with a heat-proof insulator 12 inserted therebetween and with the folded tip portion 11-1 being tapered by grinding and finished to be an earpick-like tip. When a current is conducted through the nichrome wire 11 in the direction of, for example, the arrows in FIG. 1A, the tip 11-1 having a high resistivity, is heated to be red-hot so that the tip is sterilized and a material attached thereto is burned-off. FIG. 1C provides an illustration of the current i flowing in the pick-up 10, with FIG. 1D providing an illustration of the heating temperature T of the pick-up 10. This mode is advantageous in that the temperature T can be accurately controlled by adjusting the current i and no heating furnace is required, resulting in simple arrangement of the apparatus.

Figures 2A, 2B, 2C:
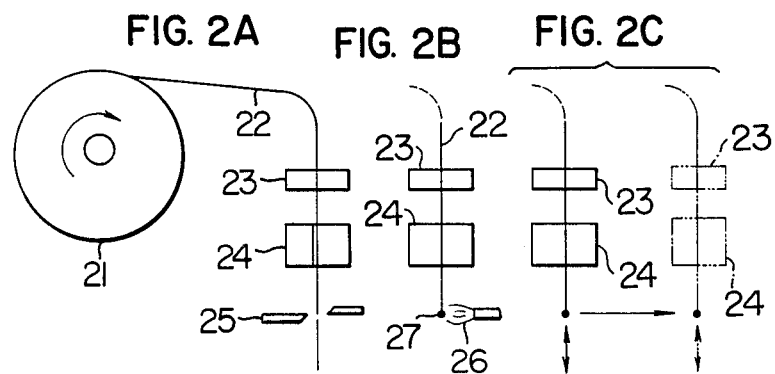
FIG. 2A–2C are schematic views of a bacterial colony pick-up/transfer end element of the disposable type suitable for use in the apparatus according to the present invention.

As shown in FIG. 1A, a thin wire 22 of a material such as, for example, gold, aluminum, glass fiber, wound on a wire reel 21, is pulled out by a feeder 23 and fixed by clamping device 24, and the ball tip or end portion 27 of the wire 22 is cut off by a cutter 25. Next, as shown in FIG. 2B, the cut end of the thin wire 22 is melted by heating by a torch flame 26 to form the ball tip 27. The bacterial colony pick-up/transfer operations are performed by using the ball tip 27 as shown in FIG. 2C. In the case of a repeating usage, the process is returned to FIG. 2A so that the end portion of the ball tip 27 is cut off and the cut end is melted by heating to form a new ball tip 27. Thus, the ball tip 27 is sterilized during the ball tip forming process while making the washing operation unnecessary. The processes for forming the melted ball tip 27 are performed through a computer control. The torch flame 26 may, for example, take the form of an electric discharge torch flame or an oxyhydrogen flame, which are maintained in an ignited state and with a direction of the torch flame 26 being controlled.

Figure 3A:
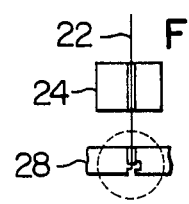
FIG. 3A–3D illustrate a method of forming a disposable element similar to that shown in FIG. 2.
Figure 3B:
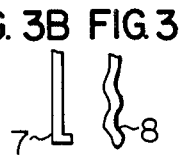
Figure 3C:
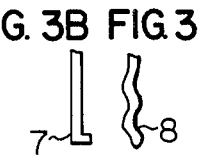
Figure 3D:
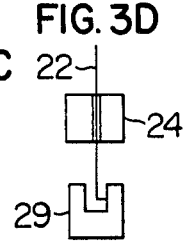

Alternatively, instead of using a melted ball tip 27, the tip of a wire 22 may, as shown most clearly in FIG. 3A, be cut off and simultaneously shaped such that the cut end portion is bent to form a bent portion 7 or 8 as shown in FIGS. 3B or C respectively, by using a cutting/shaping tool 28 and then, as shown in FIG. 3D, the bent portion 7 or 8 is subjected to heat sterilization by a heater 29 such, for example, an ordinary electric heater or a microwave heating system. Since the tip portion which has been once used is cut off, the washing operation is also not necessary in this case.

Figure 4A:
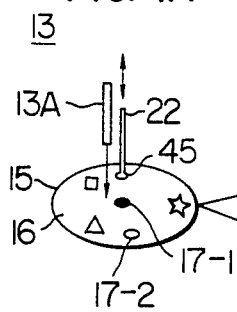
FIGS. 4A and 4B are schematic perspective views of an example of the bacterial colony transferring operation when a test Petri dish is used as the test container.

Next, the processes of automization in the bacterial colony transferring operation will be first described with respect to the case where a test Petri dish is used as a test container. More particularly, as shown in FIG. 4A, a platinum loop is used as a pick-up. Assume now that the position of a bacterial colony 17-1 selected by visual inspection by an operator, as described above, among various bacterial colonies distributed in a medium 16 in a culture Petri dish 15 has been stored in a storage device by selecting and designating the positions of colonies displayed on a display picture plane by a cursor.

Figure 4B:
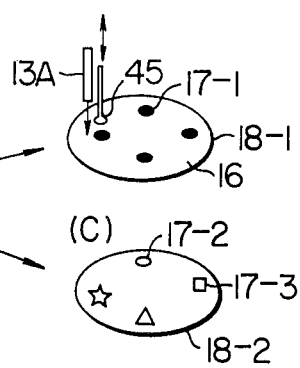

On the basis of this stored information, an X-Y stage which will be described later is moved so that the bacterial colony 17-1 is placed directly under the platinum loop or end portion 45 of the wire 22 and then the wire 22 is lowered so as to make the loop or end portion 45 contact the bacterial colony 17-1 to thereby pick up the bacterial colony 17-1 attached to the loop 45. At this time, an optical fiber, a photo diode, etc. is employed to control the height of the loop or end portion 45 so as to attain smooth contact of the loop or end portion 45 with the bacterial colony 17-1. Next, the wire 22 is pulled upward and moved by a transport mechanism, which will be described later, such that the loop or end portion 45 comes directly above a designated position by the cursor, which has stored in advance, on a medium 16 in a test Petri dish 18-1 as shown in FIG. 4B. Then the wire 22 is lowered until the loop or end portion 45 comes in contact with the medium 16 to thereby transfer the bacterial colony 17-1 to the medium 16. In order to adjust the relative positions between the loop or end portion 45 and each of the culture Petri dish and the test Petri dish, the X-Y stages on which the culture and test Petri dishes are respectively mounted are moved. The above-mentioned series of transferring operations may be readily performed under the computer control. Such control technique by a computer is well known and popularly utilized. FIG. 4B illustrates the case where the bacterial colony 17-1 of one and the same species is transferred into the test Petri dish 18-1 such that the bacterial colony 17-1 is disposed at a plurality of positions on the medium 16 in the Petri dish 18-1, it is possible, alternatively, to transfer a plurality of bacterial colonies 17-2, 17-3, etc., of various type of a plurality species into the Petri dish 18-2, as shown in FIG. 4C.

The above description applies basically to the case where the transfer is performed by using a pick-up such as shown in FIGS. 1A, 1B, 2A-2C, 3A-3D.

Next, description will be made with respect to the case when a bacterial colony is transferred from a culture Petri dish to a test tube. When a medium in the test tube is liquid, it is merely immerse the tip of pick-up in the liquid medium and therefore detailed description is omitted.

When jellized agar is employed as the medium, the following method is used in order to perform the transferring operation effectively. The method will be described by referring to FIG. 5.

The purpose of transfer into a test tube 19 is to mass produce a bacterial colony of a single species effectively, and to this end the surface of the medium in the test tube 19 is inclined with respect to the longitudinal axis of the test tube 19 so as to widen the contact area of the medium with air. Such an inclined medium surface is formed such that a medium material (agar) in the form of liquid is poured into a test tube 19 held in the properly inclined state in advance and solidified therein. Accordingly, it is possible to form the shape of medium including the angle of inclination, the height, etc. desirably and predeterminedly.

Figure 5A:
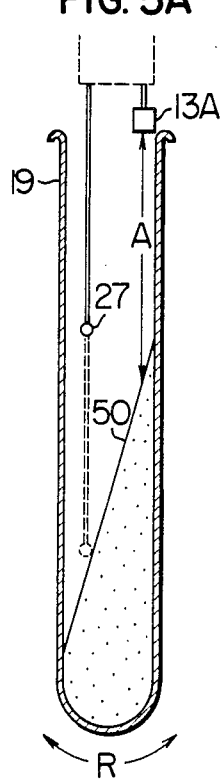
FIGS. 5A-5E are cross-sectional views of an example of the bacterial colony transferring operation when a test tube is used as the test container.

FIG. 5A shows the automatic processes of transferring a bacterial colony into the test tube 19 by using any one of a platinum loop and the pick-ups as shown in FIGS. 1A, 2 and 3. In this case, the height A as shown by arrow from the surface 50 of a medium is detected by the height sensor 13A so as to determine the direction of normal to the medium surface 50 through calculation control by the computer and after the test tube 19 has been driven by a rotary mechanism which will be described later to move in the predetermined direction and stopped thereat, the pick-up tip 27 is lowered as shown by a dotted line. Then X-Y stages on which the test tube 19 and the pick-up are respectively mounted are driven to move in connection with each other such that the tip 27 of the pick-up is moved upward from its lowered position in the zig-zag direction sliding up on the culture surface 50 to thereby scatter and transfer the bacteria, as shown in FIG. 5C.

Figure 5B:
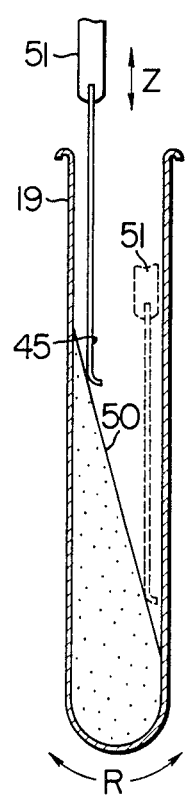
Figure 5C:
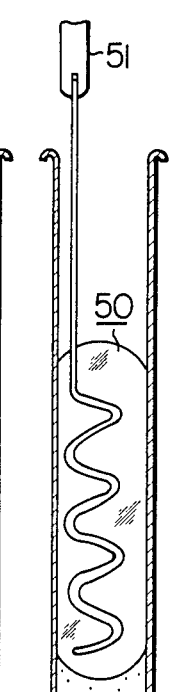

FIG. 5B provide and example of a reusable pick-up by which it is possible to detect the contact between the tip of the pick-up and the medium surface 50 by using a strain gauge 51, and in which the tip of the pick-up is stopped at a predetermined position biased from the center of the test tube 19 and being close to the inner wall of the test tube 19, by transporting means more fully described hereinbelow. If the test tube 19 is rotated in the direction indicated by arrow R and the tip of the pick-up is in contact with the medium surface 50, the contact is detected by the strain guage 51 and the rotation of the test tube 19 is stopped. At this time a lowered portion of the pick-up tip contacts the medium surface 50 as shown by a dotted line through the downward movement of the pick-up and the horizontal movement of the X-Y stage. Then, the pick-up tip moves in a zig-zag direction as shown in FIG. 5C, as described above, under the control of the computer.

Figure 5E:
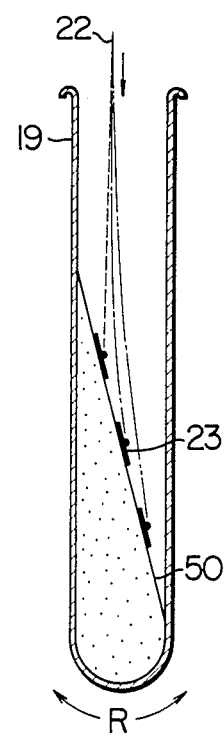
Figure 5D:
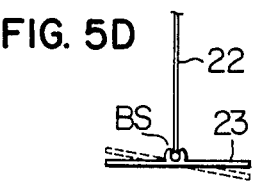

An embodiment of the bacterial colony transfer into a test tube in which a profiling plate is utilized is illustrated in the figures FIGS. 5D and 5E. More particularly, in FIG. 5D, the profiling plate 23 is attached at the tip of a flexible rod 22A through a ball-socket joint mechanism BS. Accordingly, the profiling plate 23 is pivotal freely in any inclined direction with respect to the rod 22A. The profiling plate 23 is inserted into the test tube 19 and contacts the medium surface 50. It is possible to cause the profiling plate 23 to maintain good contact with the medium surface regardless the directions of the medium surface 50 and the slide up/down while bending as shown in the drawing, thereby making it possible to perform the scattering and transferring operation through one step. Although the method of previously picking up a bacterial colony onto the under surface of the profiling plate 23 from a culture Petri dish is similar to the case where the above-mentioned various types of pick-ups are used, this case is advantageous in that a bacterial colony in a wide area can be picked up through one step by a so-called stamping operation.

Figure 6:
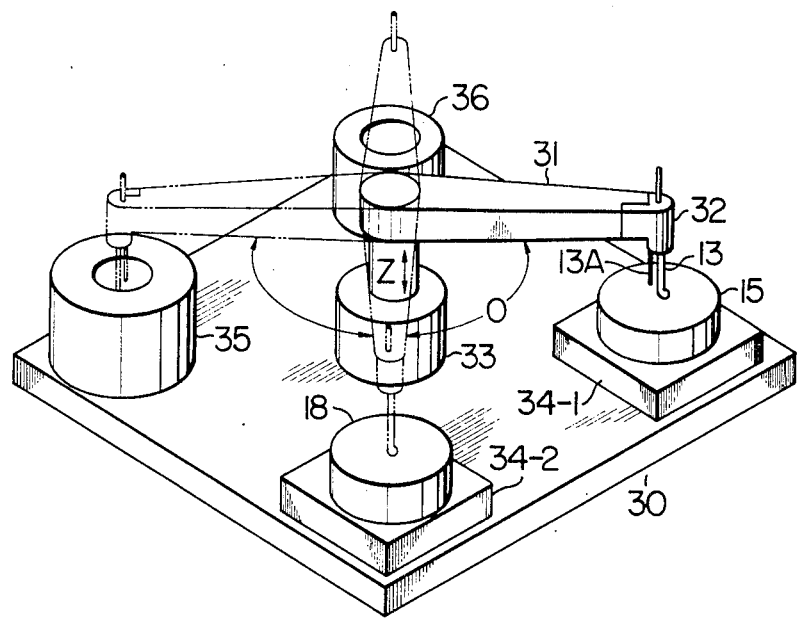
FIG. 6 is a perspective view of the bacterial colony transfer apparatus according to an embodiment of the present invention in which a bacterial colony pick-up/transfer end element which can be frequently reused.
Figure 7:
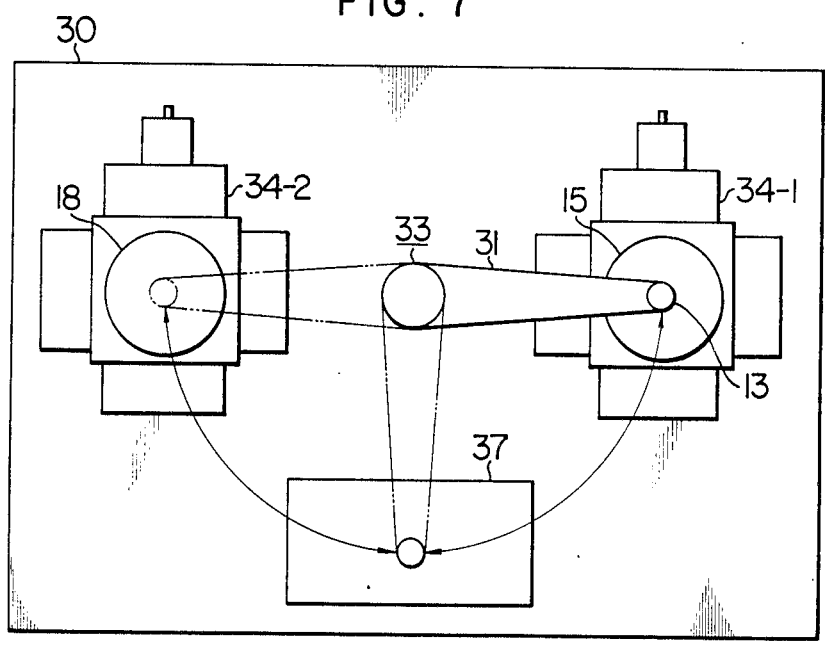
FIG. 7 is a plan view of the bacterial colony transfer apparatus according to another embodiment of the present invention in which a bacterial colony pick-up/transfer end element of the disposable type is utilized.

In FIG. 6, the bacterial colony transfer is assembled on a rigid surface table 30. An indexing head 33 is provided on central portion of the rigid surface table 30 at its central portion and a rotary arm 31 rotatable in the direction of the arrow O (FIG. 6), is attached to the indexing head 33, with the rotary arm 31 being accurately stopped at each of the four corner positions disposed 90° with respect to each other. A collet 32 is attached to the forward end of the arm 31 and the platinum loop or the reusable pick-up as shown in FIG. 1A is removably attached to the collet 32. A culture Petri dish 15 and a test Petri dish 18 are respectively mounted or X-Y stages 34-1, 34-2, so that the bacterial colony is transferred from the culture Petri dish 15 to the test petri dish 18 by the rotation and up/down movement in a Z direction of the rotary arm 31 with the Z direction, as shown in FIG. 6, being vertically disposed with respect to the X-Y stages 34-1, 34-2. All the rotation and up/down movement of the mechanism are performed under the programed control of a computer. The sterilization of the platinum loop or pick-up is performed by a sterilization section 35 and the washing and cooling are performed in a washing pit 36. Sterilization of the sterilization section 35 may be effected by using for example, a heating means, a medical fluid and optical laser. The sterilization of the embodiment in FIG. 6 is explained hereinbelow by utilizing a heating means. If a self heating type pick-up such as shown in FIG. 1A is employed, the heating section 35 and the washing pit 36 are not necessary. Further, if a pick-up having a ball tip 27 such as shown in FIGS. 2A-2C a pick-up of the type in which a thin wire 22 is cut and shaped as shown in FIGS. 3A-3D is employed, the apparatus is arranged as shown in a plan view in FIG. 7, in which the forming of the ball tip 27 or the shaping of the tip of thin wire 22 is performed at a tip or end portion processing section 37 through the processes shown in FIGS. 2A–2C or FIGS. 3A–3D, while the pick-up and transfer operations are performed in the same manner as shown in FIG. 6.

The automatic operations for melting, cutting, etc. performed in the tip or end portion processing section 37 are well known for example with respect to an automatic wire bonding machine widely employed in the art of semiconductor producing field and therefore a detailed description is omitted.

In the case where a test tube 19 is employed as a test container, it is necessary to attach a test tube stand onto the surface table 30 by using an auxiliary member since the test tube 19 is higher than a Petri dish and it is further necessary to provide a rotary mechanism because the test tube 19 must be rotated as described above.

Figure 8:
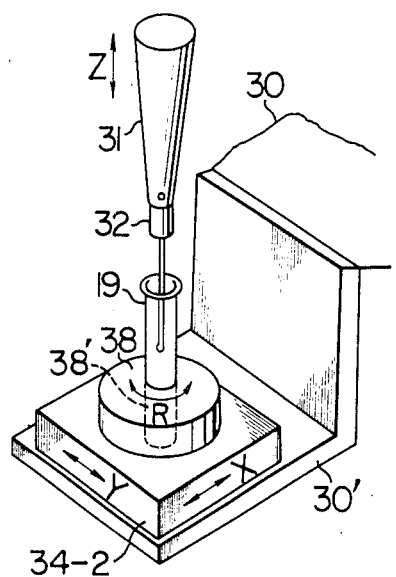
FIG. 8 is a perspective view of a part of the bacterial colony transfer apparatus according to an embodiment of the present invention in which a test tube is suitably located as the test container.

FIG. 8 provides an example of how to attach and rotate the test tube 19. More particularly, as shown in FIG. 8, an auxiliary member 30' is attached on the surface of the rigid table 30 so as to lower the vertical position of the X-Y stage 34-2 and a rotary section 38 is provided on the X-Y stage 34-2, the rotary section 38 being formed with a hole 38' into which the test tube 19 can be inserted. Although the rotary mechanism for the rotary section 38 is not shown, it will be appreciated that such a rotary mechanism as well as the mechanism for moving in the X-Y direction can be easily realized in the X direction and Y direction as shown in FIG. 8 corresponding to the X-Y movements of the X-Y stages 34-1, 34-2.

In the case where the test tube 19 is manually set such that the medium surface is made to be in a predetermined direction, it is possible, of course, that the rotary mechanism is not required so that the entire mechanism and the control therefor are remarkably simplified.

Figure 9:
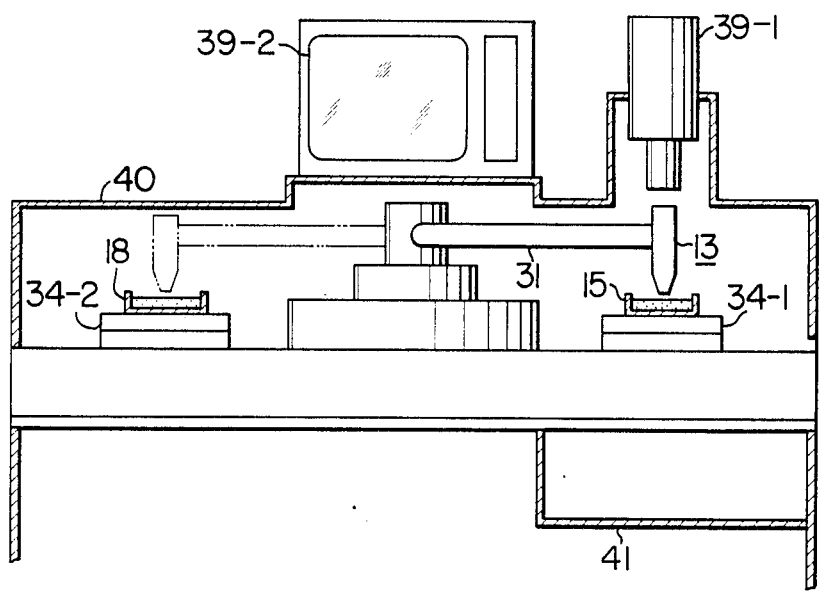
FIG. 9 is a front partial cross sectional view of the apparatus of FIG. 8.

In FIG. 9, a television camera 39-1 is attached above the culture Petri dish 15 and a monitor display 39-2 is disposed at a position suitable for monitoring by an operator. The operator may manipulate a control panel 41 to move a cursor of the monitor display 39-2 so as to select a specific bacterial colony to be transferred. A cover 40 prevents germs as well as light from entering the bacterial colony.

Figure 10:
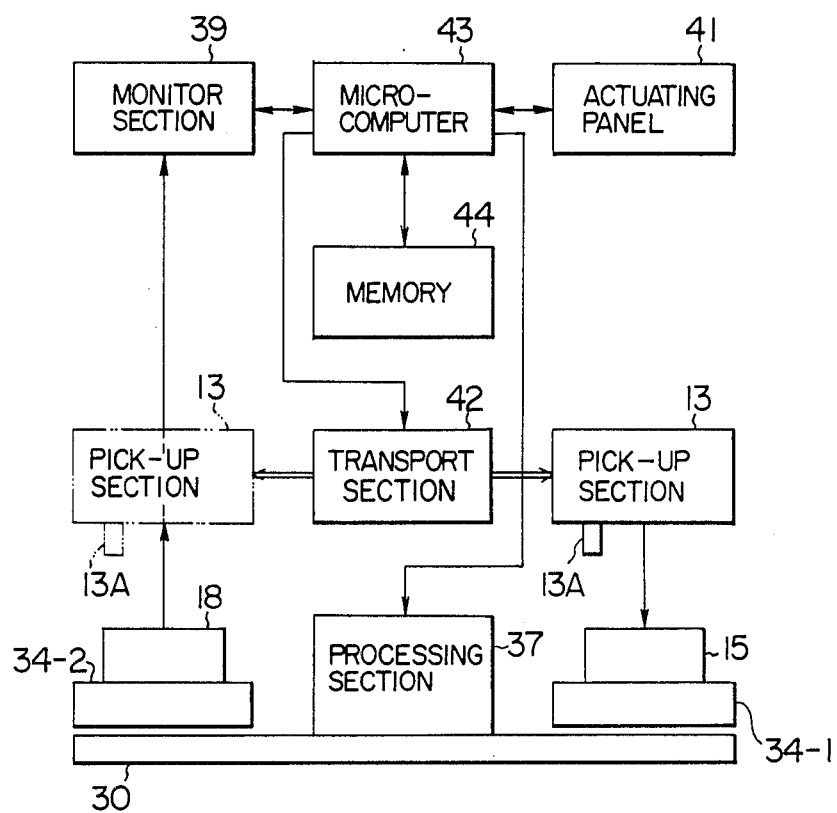
FIG. 10 is a block diagram illustrating the arrangement of an embodiment of the bacterial colony transfer apparatus according to the present invention.

In FIG. 10, a culture Petri dish 15 and a test Petri dish 18 or a test tube 19 are respectively mounted on X-Y stages 34-1 and 34-2 which are respectively disposed in a vicinity of opposite end portions of a common rigid surface table 30 and a pick-up section 13 is moved between the culture Petri dish 15 and the test Petri dish 18 or the test tube 19 by a transporting section 42 under the control of a microcomputer 43 provided with a memory 44 and an operation panel 41. A height sensor 13A provided at a pick-up section 13 detects its height from the medium surface so as to control the height of the tip of the pick-up section 13 as described above. The X-Y stages 34-1 and 34-2 may be finely moved in the two orthogonal directions, X and Y, by means of motor driving by such as a stepping motor. At an intermediate position between the X-Y stages 34-1 and 34-2, provided is an end portion processing section 37 for regenerating/sterilizing processing of the pick-up tip, for example the formation of the melted ball tip 27. The processing becomes necessary when a bacterial colony to be transferred newly selected through a monitor section 39, which will be described later, is different in type or species from the bacterial colony which has been handled so far, or when the operation is restarted after interruption, and the processing operation is performed under the control by a microcomputer 43 in conjunction with the movement of the X-Y stages. The pick-up and transfer of a bacterial colony is performed in the manner described hereinabove. The monitor section 39 includes a television camera and a display, with the television camera being mounted on the common rigid surface table 30 such that the medium surface in the culture Petri dish 15 can be well inspected.

Although a circular Petri dish is illustrated in the drawings, the shape of the container is not restricted to a circular shape but any container having a shape suitable for the automatic bacterial colony transfer apparatus such as, for example, a shape having directional quality such as a circle lacking a segment, may be of course employed.

An automatic bacterial colony transfer apparatus as described above is advantageous in that not only is skill not required for the bacterial colony transfer operation but the recording and storing of the information with respect to the bacterial colony transfer can be electronically effectively performed.

What is claimed is:

1. An automatic bacterial colony transfer apparatus comprising:

a computer with memories;

a culture container in which bacterial colonies are cultivated;

a test container into which a specific one of the bacterial colonies is transferred from said culture container;

two X-Y stages on which said culture container and said test container are respectively mounted, said X-Y stages being arranged to be independently movable of each other under the control of said computer;

a monitor section for monitoring the bacterial colonies on a surface of a medium in said culture container to observe said specific one of the bacterial colonies, said monitor section including a television camera disposed above said culture container and a display device disposed at a position suitable for observation by an operator, said television camera being provided for photographing the bacterial colonies in said culture container, said display device being provided for displaying an enlarged picture image of said colonies and said display device is also provided with a cursor for selecting said specific one of said bacteria colonies in said culture container on said display device, said memories storing information with respect to the position of said specific bacterial colony, and each of said Y-Y stages is moved in accordance with the movement of said cursor and under the control of said computer;

a pickup section having an end portion for picking up said specific bacterial colony from said culture container and for transferring the picked-up bacterial colony to a surface of a medium in said test container; and a transporting section for sequentially transporting said pick-up section between said culture and said test container under the control of said computer, whereby said specific bacterial colony is selected through said monitor section and automatically transferred from the medium of said culture container to the medium of said test container.

2. An automatic bacterial colony transfer apparatus according to claim 1, wherein said end portion includes a thin wire made of a material selected from the group consisting of gold, and glass fiber, and wherein said apparatus further comprises a pick-up processing means for drawing said thin wire out of a reel cutting off the end portion and melting the cut end of said end portion prior to transferring said specific bacterial colony from said culture container to said test container.

3. An automatic bacterial colony transfer apparatus according to claim 2, wherein said transporting section comprises a rotatably and vertically movable arm supporting said pick-up section at one end of the arm, and said pick-up processing means is disposed along a circumference of rotation of said one end of said arm.

4. An automatic bacterial colony transfer apparatus according to claim 1, in which said transporting section includes an arm pivotably mounted and arranged so as to be able to stop at four positions and vertically movably supporting said pick-up section at an end of said arm.

5. An automatic bacterial colony transfer apparatus according to claim 4, wherein said end portion includes a small flat plate attached to a tip of a flexible thin rod through a ball socket joint.

6. An automatic bacterial colony transfer apparatus according to claim 4, wherein said four positions include positions for said culture container, said test container, a heating section for heating/sterilizing said end portion, and a washing/cooling section for washing-/cooling said heated/sterilized end portion are respectively disposed.

7. An automatic bacterial colony transfer apparatus according to claim 4, further comprising strain gauge means mounted at said end portion for detecting the contact of said end portion with the surface of said medium of said test container.

8. An automatic bacterial colony transfer apparatus according to claim 1, wherein said end portion is a platinum loop.

9. An automatic bacterial colony transfer apparatus according to claim 1, wherein said end portion is a self heating type including a resistive wire which is folded in two with a heat-proof insulator material inserted therebetween, a folded tip portion of said wire having a reduced cross-sectional area.

10. An automatic bacterial colony transfer apparatus according to claim 1, wherein said culture container is a culture Petri dish and said test container is the group consisting of a test Petri dish or a test tube.

11. An automatic bacterial colony transfer apparatus according to claim 1, wherein said end portion includes a thin wire of a material selected from the group consisting of aluminum and stainless steel, and wherein said apparatus further comprises a pick-up processing means for drawing said thin wire out of a reel, cutting off and shaping said end portion, and sterilizing the cut end of said end portion, prior to a transferring of said specific bacterial colony from said culture container to said test container.

* * * * *